United States Patent [19]

Nimry et al.

[11] 4,358,582

[45] Nov. 9, 1982

[54] NOVEL NONAROMATIC DIANHYDRIDE AND POLYIMIDES FROM TRICYCLO [4.2.1.0$^{2,5}$] NONANE-3,4 DIMETHYL-3,4,7,8-TETRACARBOXYLIC ACID DIANHYDRIDE

[75] Inventors: Tayseer S. Nimry, Wheaton; Ellis K. Fields, River Forest, both of Ill.

[73] Assignee: Standard Oil Company (Indiana), Chicago, Ill.

[21] Appl. No.: 294,347

[22] Filed: Aug. 19, 1981

[51] Int. Cl.$^3$ .............................................. C08G 73/10
[52] U.S. Cl. .................................... 528/353; 528/125; 528/128; 528/188; 528/189; 528/206; 528/208; 528/220; 528/229; 528/352; 549/232; 549/234; 549/237
[58] Field of Search ................ 528/188, 189, 220, 352, 528/353, 229, 206, 208, 125, 128; 260/346.3

[56] References Cited

U.S. PATENT DOCUMENTS

| | | |
|---|---|---|
| 3,468,852 | 9/1969 | Flowers et al. ................ 528/353 |
| 3,639,356 | 2/1972 | Bradshaw ...................... 528/353 |
| 3,649,596 | 3/1972 | Smith, Jr. ...................... 528/353 |
| 3,856,752 | 12/1974 | Bateman ........................ 528/353 |
| 4,066,622 | 1/1978 | Feinstein et al. ............... 528/353 |
| 4,142,036 | 2/1979 | Feinstein et al. ............... 528/188 |
| 4,271,079 | 6/1981 | Maeda et al. ................... 528/353 |
| 4,271,288 | 6/1981 | Woo .............................. 528/188 |

*Primary Examiner*—Lester L. Lee
*Attorney, Agent, or Firm*—Gunar J. Blumberg; William T. McClain; William H. Magidson

[57] ABSTRACT

Novel polyimides and molding compositions are prepared from novel tricyclo[4.2.1.0$^{2,5}$] nonane-3,4 dimethyl-3,4,7,8-tetracarboxylic acid dianhydride. The dianhydride is useful for the manufacture of polyimides which are useful as engineering plastics.

26 Claims, No Drawings

NOVEL NONAROMATIC DIANHYDRIDE AND POLYIMIDES FROM TRICYCLO [4.2.1.0$^{2,5}$] NONANE-3,4 DIMETHYL-3,4,7,8-TETRACARBOXYLIC ACID DIANHYDRIDE

BACKGROUND OF THE INVENTION

1. Field of the Invention

The field of this invention relates to novel nonaromatic dianhydrides and to polyimides and copolyimides prepared from the novel nonaromatic dianhydrides or mixtures of these with other dianhydrides. Tricyclo[4.2.1.0$^{2,5}$]nonane-3,4-dimethyl-3,4,7,8-tetracarboxylic acid dianhydride (I) is a novel compound. I is used to prepare novel polyimides which are useful in preparing molded articles, fibers, laminates and coatings.

2. Background

British Patent Specification 570,858 discloses various processes for making fiber forming polymers. The prior art does not disclose or contemplate I nor the polyimides prepared from I which are useful as moldings, fibers, laminates and coatings.

The general object of this invention is to provide novel polyimides and copolyimides based on the new dianhydride I and one or more diamine moieties. A more specific object of this invention is to provide polyimides from I and aliphatic, cycloaliphatic, araliphatic and aromatic diamine moieties. It is also suitable to use a mixture of I and another aromatic or aliphatic dianhydrides to manufacture copolyimides.

We have found that novel polyimides can be formed by reacting I with diamines. I reacts readily with the diamine to form a high molecular weight polyimide. In the novel process both aliphatic and aromatic diamines can be polymerized with I in the melt to form high molecular weight polyimides and copolyimides.

Our process for the manufacture of the novel polyimides and copolyimides comprises reacting about equal molar amounts of I with a primary diamine or a mixture of primary diamines. The molecular ratio of I to the primary diamine may be in the range of 1.2 to 1 preferably in the range of 1 to 1. In suitable method, the reaction is conducted as a batch reaction at a temperature of about 130° to 300° C. for a period of about 2 to 8 hours in a nitrogen containing organic polar solvent such as N-methyl-2-pyrrolidinone, N,N-dimethylacetamide or pyridine. I can be replaced partially by another dianhydride either aromatic or aliphatic.

The other dianhydrides are characterized by the following formula:

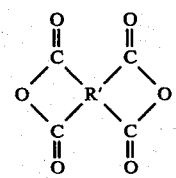

wherein R' is a tetravalent organic radical selected from the group consisting of aromatic, aliphatic, cycloaliphatic, heterocyclic, combination of aromatic and aliphatic, and substituted groups thereof. However, the preferred dianhydrides are those in which the R' groups have at least 6 carbon atoms, wherein the 4 carbonyl groups of the dianhydride are each attached to separate carbon atoms and wherein each pair of carbonyl groups is directly attached to adjacent carbon atoms in the R' group to provide a 5-membered ring as follows:

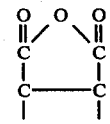

The preferred dianhydrides, as recited above, yield upon reaction with the diamines polyimide structures having outstanding physical properties. Illustrations of dianhydrides suitable for use in the present invention include: pyromellitic dianhydride; 2,3,6,7-naphthalene tetracarboxylic dianhydride; 3,3',4,4-diphenyl tetracarboxylic dianhydride; 1,2,5,6-naphthalene tetracarboxylic dianhydride; 1,2,3,4-cyclopentane tetracarboxylic dianhydride; 2,2',3,3'-diphenyl tetracarboxylic dianhydride; 2,2-bis(3,4-dicarboxyphenyl)propane dianhydride; 2,3,4,5-pyrrolidine tetracarboxylic dianhydride; 3,4,9,10-perylene tetracarboxylic dianhydride; bis(3,4-dicarboxyphenyl)ether dianhydride; ethylene tetracarboxylic dianhydride; 3,3',4,4'-benzophenonetetracarboxylic dianhydride; bis(3,4-dicarboxyphenyl)sulfide dianhydride; bis(3,4-dicarboxyphenyl)sulfone dianhydride; bis(3,4-dicarboxyphenyl)methane dianhydride; 1,4,5,8-naphthalenetetracarboxylic dianhydride; tricyclo[4,2,2,0$^{2,5}$]dec-7-ene-3,4,9,10-tetracarboxylic dianhydride; 3,6-ethenohexahydropyromellitic dianhydride; cyclobutane-1,2,3,4-tetracarboxylic dianhydride; and 1,3-dimethylcyclobutane-1,2,3,4-tetracarboxylic dianhydride. The polycondensation can also be carried out as a continuous process. The polycondensation can suitably be carried out at a temperature of 130° C. to 300° C., preferably at a temperature of 180° to 250° C. The novel polyimides of this invention have the following recurring structure wherein R is a divalent aliphatic or aromatic hydrocarbon radical.

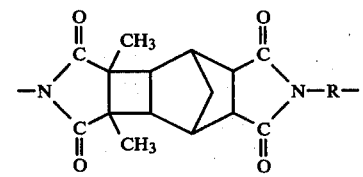

The radical R may be a divalent aliphatic hydrocarbon of 2 to 18 carbon atoms or an aromatic hydrocarbon from 6 to 20 carbon atoms, or an aromatic hydrocarbon radical containing from 6 to 10 carbon atoms joined directly or by stable linkage comprising —O—, methylene,

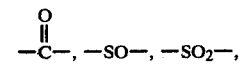

and —S— radicals. The radical R is derived from aliphatic, araliphatic or cycloaliphatic diamines such as ethylenediamine, propylenediamine, 2,2-dimethylpropylene diamine, tetramethylene diamine, hexamethylene diamine, octamethylene diamine, nonamethylene diamine, decamethylene diamine, dodecamethylene diamine, 4,4'-diaminodicyclohexylethane, xylylene diamine and bis(aminomethyl)cyclohexane. Suitable aromatic diamines useful in our process include para- and meta-phenylenediamine, 4,4'-oxydianiline, thiobis(aniline), sulfonylbis(aniline), diaminobenzophenone, methylenebis(aniline), benzidine, 1,5-diaminonaphthalene, oxybis(2-methylaniline), thiobis(2-methylaniline), and the like. Examples of other useful aromatic primary diamines are set out in U.S. Pat. No. 3,494,890 (1970) and U.S. Pat. No. 4,016,140 (1972) both incorporated herein by reference. The preferred diamines are hexamethylene diamine and dodecamethylene diamine.

In some cases the polyimide may be further polymerized under "solid state polymerization" conditions. The term solid state polymerization refers to chain extensions of polymer particles under conditions where the polymer particles retain their solid form and do not become a fluid mass. The solid state polymerization can be carried out below the melting point of the polyimide and can be conducted in several ways. However all techniques require heating the ground or pelletized polyimide below the melting point of the polyimide, generally at a temperature of about 175° to 300° C. while either sparging with an inert gas such as nitrogen or operating under vacuum. In cases where the polyimides and copolyimides have a low melt temperature, they can be polymerized in the melt under vacuum in thin sections or using thin film reactors known in the art.

Injection molding of the novel polyimide is accompanied by injecting the polyimide into a mold maintained at a temperature of about 25° C. to 150° C. In this process a 20 second to 1 minute cycle is used with a barrel temperature of about 125° C. to 350° C. The latter will vary depending on the $T_g$ of the polymer being molded. The injection molding conditions are given in Table 1.

TABLE I

| Mold Temperature | 25 to 150° C. |
|---|---|
| Injection Pressure | 15,000 to 19,000 psi and held for 1 to 3 seconds |
| Back Pressure | 100 to 220 psi |
| Cycle Time | 25 to 28 seconds |
| Extruder: | |
| Nozzle Temperature | 125° C. to 350° C. |
| Barrels: | |
| Front heated to | 125° C. to 350° C. |
| Screw: | |
| 20 to 25 revolutions/minute | |

The novel polyimides have excellent mechanical and thermal properties and can readily be molded into useful articles or formed into fibers, films, laminates or coatings.

Infrared spectra of the polyimides have confirmed the polyimide structure.

Analysis of the polyimides by thermal gravimetric analysis shows excellent stability. Glass transition temperature Tg of the polyimides varied with the particular diamine used. Values range from a Tg of 65° C. to 115° C.

Diamines with the amino groups attached directly to the aromatic ring are suitably polymerized with I by solution condensation in organic polar solvents. They include N,N-dimethylacetamide, N-methyl-2-pyrrolidinone, N,N-dimethylformamide, pyridine, and the like.

The following examples illustrate the preferred embodiment of the invention. It will be understood that the examples are for illustrative purposes only and do not purport to be wholly definitive with respect to conditions or scope of the invention.

EXAMPLE 1

Synthesis of Tricyclo[4.2.1.0$^{2,5}$]Nonane-3,4-Dimethyl-3,4,7,8-Tetracarboxylic Acid Dianhydride (I)

I of the following structure:

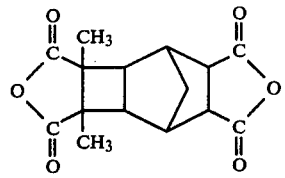

is prepared by a photocycloaddition reaction between dimethylmaleic anhydride (II) and 5-norbornene-2,3-dicarboxylic anhydride (III). To a 500-ml pyrex erlenmeyer flask equipped with a condenser was added 5.0 g (40 mmole) of II, 6.51 g (40 mmole) of III and 0.3 g of benzophenone. The mixture was dissolved in 100 ml toluene and exposed to light from a GE sunlamp for 64 hours. During this time the insoluble photodimer of II was filtered off at several intervals. At the end of the irradiation the filtrate was concentrated to approximately 50 ml on a rotary evaporator. I precipitated and was collected and washed with a small volume of cold toluene. Approximately one half of II dimerized to the useful tetramethylcyclobutane tetracarboxylic dianhydride.

The yield of I based on the remaining dimethylmaleic anhydride was 30%. Its melting point after recrystallization from acetone is 315°–8° C. (dec.) Anal. Calcd. for $C_{15}H_{14}O_6$: C, 62.07, H, 4.83. Found: C, 62.35; H, 4.95.

The mass spectrum recorded at a probe temperature of approximately 220° C. is consistent with the proposed configuration for I. A partial list of the ions detected is shown here:

| | Mass | Ion Identification | Fragmentation |
|---|---|---|---|
| | 290 | $C_{15}H_{14}O_6$ | I$^+$, molecular ion |
| | 275 | $C_{14}H_{11}O_6$ | I—CH$_3$ |
| | 272 | $C_{15}H_{12}O_5$ | I—H$_2$O |
| | 262 | $C_{14}H_{14}O_5$ | I—CO |
| | 245 | $C_{14}H_{13}O_4$ | I—COOH |
| | 244 | $C_{14}H_{12}O_4$ | I—CO—H$_2$O |
| | 234 | $C_{13}H_{14}O_4$ | I—CO—CO |
| (base peak) | 218 | $C_{13}H_{14}O_3$I | I—CO—CO$_2$ |

EXAMPLE 2

Dianhydride I was crystallized from acetone and dried at 120° C. for 18 h. Dodecamethylene diamine (DDA) was distilled under vacuum. DDA, 2.0 g (0.01 mol) was placed in the reaction flask and dissolved in 30 ml of N-methyl-2-pyrrolidinone (NMP) while purging with nitrogen. Compound I, 2.9 g (0.01 mol) was then added all at once and the addition funnel was washed into the flask with another 15 ml of NMP. The mixture was stirred at 25° C. for 1 h, 100° C. for 1 h, and 150° C. for 1 h. At this temperature, 20 ml of NMP were distilled off with most of the water byproduct. The solution which at this point became viscous was heated at 250° C. for 3 h. After cooling to 25° C. the polymer solution was mixed with water in a blender. The polyimide was filtered, washed with water and dried in a vacuum oven at 150° C. for 20 h. Nitrogen Analysis: Calcd. for $C_{27}H_{38}N_2O_4$: 6.2%. Found: 6.0%.

Measurement of the inherent viscosity (I.V.) for this polymer and all polymers in the following examples was carried out on a solution made by dissolving 0.1 g of the polymer in 25 ml of a 60/40 mixture of phenol/tetrachloroethane at 130° C. then cooling to 30° C., the temperature at which the measurement was made. I.V. for the polyimide of Example 2 was 0.92 dl/g.

EXAMPLE 3

Another reaction was carried out between I and DDA as in Example 2. The polyimide formed had an I.V. of 0.32, and a nitrogen content of 6.4%. A molded specimen had a Tg of 68° C. and ultimate tensile strength of 5220 psi.

EXAMPLE 4

Using 4.35 g (0.015 mol) of I and 1.74 g (0.015 mol) of hexamethylene diamine in 60 ml of NMP, a polyimide was prepared according to Example 2. Nitrogen Analysis: Calcd. for $C_{21}H_{26}N_2O_4$: 7.7%. Found: 8.1%. The polyimide had an I.V. of 0.32. A molded specimen showed the following properties: Tg, 112° C.; yield tensile strength, 8720 psi; ultimate tensile strength, 7200 psi; tensile impact strength, 17 ft-lbs/in$^2$; and % elongation, 70.

We claim:

1. A polyimide consisting essentially of the following recurring structure:

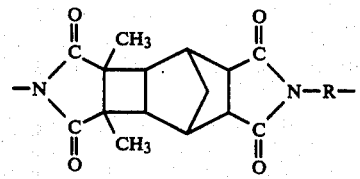

wherein R is a divalent aliphatic, cycloaliphatic, araliphatic or aromatic hydrocarbon radical.

2. The polyimide of claim 1 wherein R is an aliphatic hydrocarbon from 2 to 18 carbon atoms.

3. The polyimide of claim 1 wherein R is an aromatic hydrocarbon from 6 to 20 carbon atoms.

4. The polyimide of claim 1 wherein the aromatic hydrocarbon radical contains from 6 to 10 carbon atoms joined directly or by stable linkage selected from the group consisting essentially of —O—, methylene,

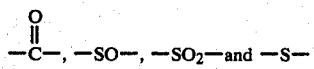

radicals.

5. The polyimide of claim 1 wherein the polyimide is in the form of a molded object.

6. The polyimide of claim 1 wherein the polyimide is in the form of a fiber.

7. The polyimide of claim 1 wherein the polyimide is in the form of a film.

8. The polyimide of claim 1 wherein the polyimide is in the form of a metal coating suitable for electrical service.

9. A polyimide consisting essentially of the following recurring structure:

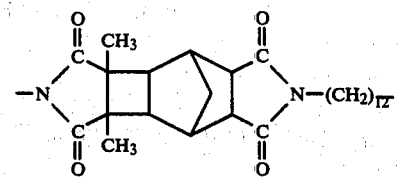

10. A polyimide of claim 9 wherein the polyimide is in the form of a molded object.

11. The polyimide of claim 9 wherein the polyimide is in the form of a fiber.

12. The polyimide of claim 9 wherein the polyimide is in the form of a film.

13. A polyimide consisting essentially of the following recurring structure:

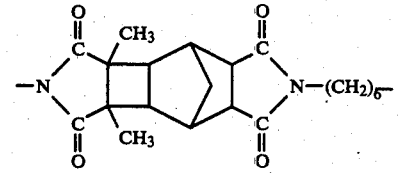

14. A polyimide of claim 13 wherein the polyimide is in the form of a molded object.

15. The polyimide of claim 13 wherein the polyimide is in the form of a fiber.

16. The polyimide of claim 13 wherein the polyimide is in the form of a film.

17. A copolyimide consisting essentially of the following recurring structure

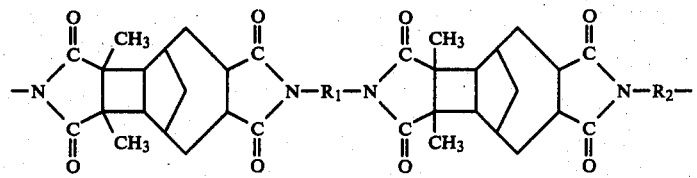

wherein $R_1$ and $R_2$ are different divalent aliphatic, cycloaliphatic, araliphatic or aromatic hydrocarbon radicals.

18. The copolyimide of claim 17 wherein $R_1$ and $R_2$ are aliphatic hydrocarbons from 2 to 18 carbon atoms.

19. The copolyimide of claim 17 wherein $R_1$ and $R_2$ are aromatic hydrocarbons from 6 to 20 carbon atoms.

20. The copolyimide of claim 17 wherein the polyimide is in the form of a molded object.

21. The copolyimide of claim 20 wherein the aromatic hydrocarbon radicals contain from 6 to 10 carbon atoms joined directly or by stable linkage selected from the group consisting essentially of —O—, methylene,

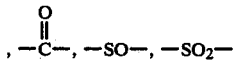

and —S— radicals.

22. The copolyimide of claim 17 wherein the polyimide is in the form of a fiber.

23. The copolyimide of claim 17 wherein the polyimide is in the form of a film.

24. A copolyimide consisting essentially of the following recurring structure:

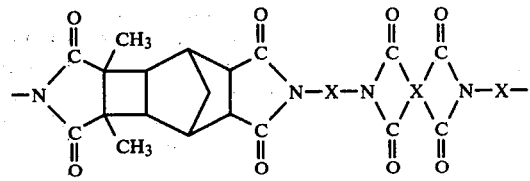

wherein X is a divalent hydrocarbon radical and X' is a tetravalent hydrocarbon radical.

25. The copolyimide of claim 24 wherein X and X' are aliphatic hydrocarbons from 2 to 18 carbon atoms.

26. The copolyimide of claim 24 wherein X and X' are aromatic hydrocarbons of 6 to 20 carbon atoms.

* * * * *

UNITED STATES PATENT OFFICE
CERTIFICATE OF CORRECTION

Patent No. 4,358,582　　　　　　　　　Dated November 9, 1982

Inventor(s) Tayseer S. Nimry and Ellis K. Fields

It is certified that error appears in the above-identified patent and that said Letters Patent are hereby corrected as shown below:

| Col. | Line | | |
|---|---|---|---|
| 2-3 | 68-1 | "para- and meta-" | --para- and meta- -- |
| 4 | 50 | "$C_{13}H_{14}O_{31}$" | --$C_{13}H_{14}O_3$-- |
| 4 | 64 | "byproduct" | --by-product-- |
| 5 | 6-7 | "phenol/-tetrachlorethane" | --phenol/tetrachlorethane-- |

Signed and Sealed this

Twentieth Day of September 1983

[SEAL]

Attest:

Attesting Officer

GERALD J. MOSSINGHOFF

Commissioner of Patents and Trademarks